United States Patent
Fujioka et al.

(10) Patent No.: US 6,336,923 B1
(45) Date of Patent: *Jan. 8, 2002

(54) DISPOSABLE DIAPERS

(75) Inventors: Yoshihisa Fujioka, Kagawa-ken; Hirotomo Mukai, Ehime-ken, both of (JP)

(73) Assignee: Uni-Charm Corporation, Ehime-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/105,617

(22) Filed: Aug. 13, 1993

(30) Foreign Application Priority Data

Aug. 24, 1992 (JP) ............................... 4-224342

(51) Int. Cl.[7] ............................ A61F 13/15; A61F 13/20
(52) U.S. Cl. ...................... 604/394; 604/397; 604/402
(58) Field of Search ............................ 604/358, 385.1, 604/385.2, 386, 387, 392–396, 402; 2/400, 401, 403, 404, 406, 407; 607/397

(56) References Cited

U.S. PATENT DOCUMENTS

| 2,492,620 | A | * | 12/1949 | Cohen | ........................ 604/395 |
|---|---|---|---|---|---|
| 2,654,367 | A | | 10/1953 | Turnham | |
| 3,828,785 | A | * | 8/1974 | Gamm et al. | ................ 604/394 |
| 3,860,003 | A | | 1/1975 | Buell | |
| 3,981,306 | A | * | 9/1976 | Krusko | |
| 4,019,517 | A | * | 4/1977 | Glassman | |
| 4,022,210 | A | * | 5/1977 | Glassman | ..................... 604/394 |
| 4,205,679 | A | * | 6/1980 | Repke et al. | ................ 604/394 |
| 4,244,367 | A | * | 1/1981 | Rollenhagen | ................ 604/396 |
| 4,425,130 | A | * | 1/1984 | DesMarais | |
| 4,427,408 | A | * | 1/1984 | Karami et al. | ................ 604/393 |
| 5,451,217 | A | * | 9/1995 | Fujioka et al. | ................ 604/393 |
| 5,746,730 | A | * | 5/1998 | Suzuki et al. | ................ 604/393 |

FOREIGN PATENT DOCUMENTS

| FR | A2517524 | | 10/1983 |
|---|---|---|---|
| FR | A2517525 | | 10/1983 |
| GB | 2256803 | * | 12/1992 |
| JP | 52-40267 | | 10/1977 |

* cited by examiner

Primary Examiner—Aaron J. Lewis
Assistant Examiner—K. M. Reichle
(74) Attorney, Agent, or Firm—Lowe Hauptman Gilman & Berner, LLP

(57) ABSTRACT

A disposable diaper has front and a rear bodies permanently welded together at a crotch zone along a welding line convexly curved upward. Fasteners are formed along side edges of one of the front and rear bodies to enable the bodies to be releasably attached together to form the basic structure of the diaper. An auxiliary liquid absorbent panel is permanently attached to float above the convexly curved welding line of the crotch zone for greater absorbency.

5 Claims, 1 Drawing Sheet

DISPOSABLE DIAPERS

BACKGROUND OF THE INVENTION

The present invention relates to a disposable diaper.

A typical example of the open type disposable diaper having tape fastener means used to fasten front and rear bodies to each other at the level of the waist line is disclosed in Japanese Patent No. 1977-40267. This example comprises a liquid-permeable topsheet, a liquid-impermeable backsheet, and a liquid-absorbent panel sandwiched therebetween, wherein a pair of side flaps are formed by portions of the top- and backsheets extending outward beyond laterally opposite sides of the panel, and the respective side flaps are formed at a crotch level with cutouts destined to define leg-openings around which the respective side flaps are provided with elastic members serving to seal the side flaps around the respective legs of the wearer and wherein the rear body is provided at laterally opposite sides thereof with tape fasteners used to fasten the rear body to the front body.

As the diaper disclosed in the above-identified Japanese Patent No. 1977-40267 is typical, the cutouts formed in opposite sides of the crotch zone for improving the fitness of the diaper to the wearer's body necessarily reduce the width of the crotch zone and it is practically impossible for the crotch zone to thoroughly surround the wearer's thighs. The crotch zone thus width-reduced inevitably decreases the ability of the crotch zone to absorb liquid excretion, particularly when liquid excretion readily occurs along opposite side edges of the crotch zone.

Generally, in the well known diaper of the type as disclosed in the above-identified Japanese Patent, a fold line of the crotch zone corresponding to a boundary line of front and rear bodies horizontally extends parallel to the waist line. In addition, the liquid-absorbent panel has so-called semi-rigidity, since it often comprises a more or less compressed accumulation of fluff pulp and tissue papers covering top- and bottom surfaces of this accumulation. Accordingly, a crotch zone of the diaper can not fit the corresponding zone of the wearer's body, thus not only giving the wearer a feeling of incompatibility but also causing leakage of excretion.

SUMMARY OF THE INVENTION

In view of the problem as mentioned above, it is a principal object of the invention to provide a disposable diaper having a crotch zone configured so as to combine the advantage of an open type diaper with the advantage of a short-pants type diaper that has thoroughly covering portions surrounding the legs of a wearer and thereby eliminates the drawbacks of the well known diaper as mentioned above.

The advantage of the open type diaper lies in that the diaper can be adjustably tightened around a waist-opening as well as around leg-openings and the advantage of the short-pants type diaper lies in that the diaper has hoses to cover at least inner sides of the wearer's thighs and the crotch zone can be dimensioned to be larger than that in the well known diaper.

To achieve the object set forth above, the invention generally resides in a disposable diaper comprising front and rear bodies, characterized by that said front and rear bodies are separately formed and welded together adjacent lower ends along a welding line convexly curved toward the waist line of said front and rear bodies so as to define a crotch zone, wherein an auxiliary liquid-absorbent panel that is elongated longitudinally with respect to said front and rear bodies is bonded at least at longitudinally opposite ends thereof to the top surface of said crotch zone. The auxiliary liquid-absorbent panel, in a preferred embodiment, is positioned in the crotch zone and mounted so as to float at a spaced distance from the welding line of the convexly curved crotch zone.

Preferably, said crotch zone defined by said convexly curved welding line is formed along its outer edges with a correspondingly curved cutout.

With the article constructed according to the invention as outlined above, the auxiliary liquid-absorbent panel is reliably centered to the wearer's crotch and laterally opposite sides of the crotch zone cover at least the inner sides of wearer's thighs. In this manner the crotch zone of the diaper covers substantially the entire crotch of the wearer.

BRIEF DESCRIPTION OF THE DRAWINGS

The invention will be described by way of example in reference with the accompanying drawings, in which:

FIG. 1 is a front view showing an embodiment of a diaper constructed according to the teachings of the invention; and FIG. 2 is a schematic sectional view taken along a line X—X in FIG. 1.

DESCRIPTION OF THE PREFERRED EMBODIMENTS

Figures 1, 2:
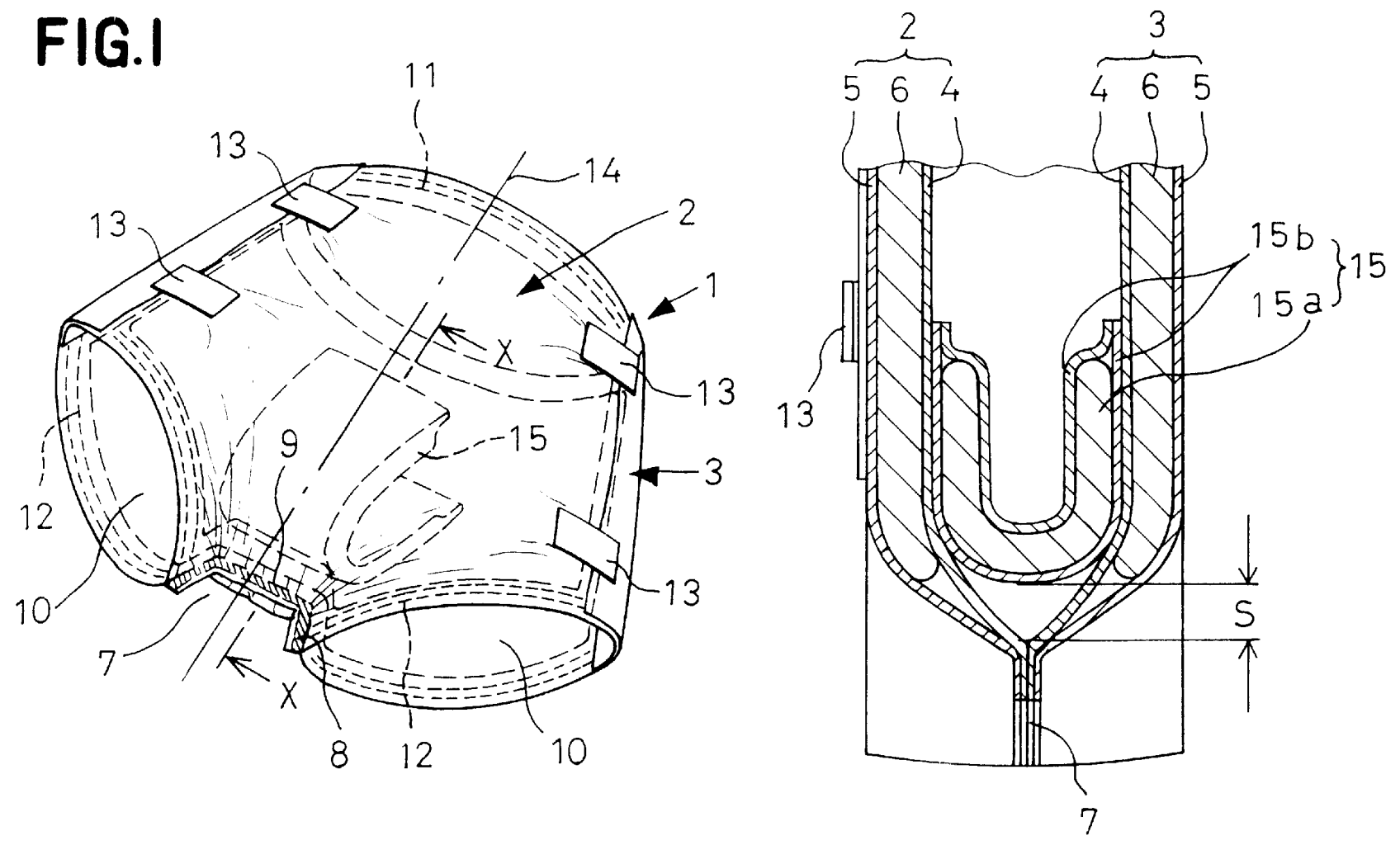

Referring to FIGS. 1 and 2, a diaper's basic structure 1 generally comprises front and rear bodies 2, 3. The rear body 3 is transversely dimensioned to be larger than the front body 2. Each of front and rear bodies 2, 3 comprises a liquid-permeable topsheet 4, a liquid-impermeable backsheet 5 and a liquid-absorbent panel 6 sandwiched between said top- and backsheets 4, 5.

Lower ends of front and rear bodies 2, 3 are formed at their middle positions with cutouts 7 convexly curved toward the waist lines of the front and rear bodies 2, 3. The front and rear bodies 2, 3 are welded together along a heat sealed supersonic welding line 8 extending parallel with the cutouts 7 so as to leave narrow edges of the cutouts 7 not welded. The size, shape and curvature radius of the welding line 8 may be appropriately selected depending on whether the diaper is for an adult or for a baby so far as the welding line 8 is convexly curved toward the waist line of the front and rear bodies 2, 3 and at least the inner sides of the leg-openings 10 extend downward beyond the apex 9 of the convexly curved welding line 8.

Circumferentially stretchable elastic members 11, 12 are interposed between the edges of the top- and backsheets 4, 5 extending beyond the panel 6 around the waist and leg-openings, respectively, and said edges are closed together by a hot melt type adhesive or said welding means. Laterally opposite side edges of the top- and backsheets 4, 5 extending beyond the panel 6 are also closed together in the same manner and the rear body 3 is provided on laterally opposite side edges with a plurality of fastener means 13, each comprising a tape fastener applied on one side with pressure-sensitive adhesive, by which the laterally opposite sides of the rear body 3 are fastened to the corresponding sides of the front body 2.

While laterally opposite side edges and lower edges around the respective leg-openings of front and rear bodies 2, 3 are illustrated as extending neither parallel with nor perpendicularly to a vertical axis 14, these side edges may extend parallel with the vertical axis 14 and these lower edges around the respective leg-openings may extend perpendicularly to said vertical axis 14 within the scope of the invention.

The diaper's basic structure 1 is provided on the top surface of its crotch zone with an auxiliary liquid-absorbent panel 15 which is elongate longitudinally of the diaper's basic structure 1. The auxiliary panel 15 comprises a liquid-absorbent core 15*a* covered with liquid-permeable sheets 15*b* and is bonded at least at longitudinally opposite ends to the top surface of the topsheet 4 by means of adhesive. With the diaper's basic structure 1 being put on a wearer, the auxiliary panel 15 is curved in a U-shape together with the diaper's basic structure 1. The auxiliary panel 15 is preferably bonded to the diaper's basic structure 1 in a manner such that the auxiliary panel 15 thus curved floats above the top surface of the basic structure's crotch zone and more specifically the curved auxiliary panel 15 has its outer bottom spaced by a distance S of at least 10 mm from the top surface of the basic structure's crotch zone. However, it is also possible within the scope of the invention to arrange the auxiliary panel 15 so that the bottom of the auxiliary panel 15 may remain in contact with the top surface of the diaper's crotch zone even in the curved state.

The auxiliary panel 15 may have its bottom layer comprising a liquid-impermeable sheet and/or have stretchable side flaps extending from laterally opposite sides thereof without departure from the scope of the invention.

The diaper's basic structure 1 is opened at the laterally opposite sides, therefore, at the waist-opening as well as the leg-openings and, after being joined with use of the fastener means as illustrated by FIG. 1, the laterally opposite sides are closed, and as a consequence the waist-opening as well as the leg-openings are also closed. The sizes of these openings depend on the overlap width of the front and rear bodies 2, 3 and the overlap width depends, in turn, on the sizes of an individual wearer's waist and legs (thighs).

Components of the diaper 1 may be made from materials commonly used in the well known diaper. For example, the topsheet 4 may be made of nonwoven fabric, the backsheet 5 may be made of plastic film, the panel 6 may be made of fluff pulp mixed with superabsorbent polymer, the elastic members 11, 12 may be made of natural or synthetic rubber, and substrate of the fastener means 13 may be made of fine quality paper or laminate of nonwoven fabric and plastic film. The core 15*a* of the panel 15 may be made of fluff pulp mixed with superabsorbent polymer and the sheet 15*b* covering the core 15*a* may be made of nonwoven fabric.

With the diaper constructed according to the invention as described above, the formation of the cutouts in opposite sides of the crotch zone so as to define the leg-openings never results in unacceptably narrow width of the crotch zone, since the welding line convexly curved toward the waist line allows the width of the crotch zone defined between the opposite side edges of the crotch zone to be dimensioned adequately large. In addition, the formation of such welding line allows the crotch zone to cover at least the inner sides of the thighs and the provision of the auxiliary liquid-absorbent panel over the crotch zone allows the crotch zone to absorb liquid excretion sufficiently to prevent any liquid excretion from leaking along the laterally opposite side edges of the crotch zone since the absorbent material exists on the welding line along which the separately formed front and rear bodies are welded together.

What is claimed is:

1. Disposable absorbent pants comprising a front body (2), a rear body (3) and a liquid absorbent panel (15) disposed between said front body (2) and said rear body (3), said pants further having a waist opening, two leg openings (10) and a crotch area extending between said leg openings (10), (a) each said body (2, 3) comprised of a liquid-permeable topsheet (4), a liquid-impermeable backsheet (5) and a mass of absorbent material (6) sandwiched therebetween, (b) each body (2, 3) having spaced apart side edges, each side edge of said front body (2) being detachably joined in overlapping relationship to a side edge of said rear body (3) by a plurality of fasteners (13), (c) each body (2, 3) having bottom edges, portions of the bottom edges of said bodies (2,3) being spaced apart from each other to form leg openings (10) and the remaining portions of the bottom edges of said bodies (2,3) being bonded together along a convexly curved welding line (8) to thereby form a convexly curved crotch zone that extends between said leg openings (10), said convexly curved crotch zone having an apex (9) that is closer to said waist opening than are said leg openings (10), (d) said liquid-absorbent panel (15) having a generally U-shaped configuration
      (i) that is positioned in said crotch zone and permanently attached to each topsheet,
      (ii) open ends of said U-shaped configuration facing toward said waist opening,
      (iii) a closed end of said U-shaped configuration being mounted so that a lowermost portion of the closed end facing downward towards the bonded together bodies along the welding line (8) is spaced above the bonded together bodies along the welding line (8) so as to float at a spaced distance from said convexly curved welding line (8) of said convexly curved crotch zone.

2. The pants of claim 1, wherein said liquid absorbent panel includes a core sandwiched between a pair of sheets permanently attached to each other.

3. The pants of claim 2, wherein an outer one of said sheets includes two generally straight portions interconnected with a bent portion to define said U-shaped configuration, such straight portions each being in contact with opposing regions of said top sheets along substantially the entire surface areas of said straight regions.

4. The pants of claim 1, wherein the floating panel is substantially co-elevationally adjacent said absorbent material.

5. Disposable absorbent pants comprising a front body (2), a rear body (3) and a liquid absorbent panel (15) disposed between said front body (2) and said rear body (3), said pants further having a waist opening, two leg openings (10) and a crotch area extending between said leg openings (10), (a) each said body (2, 3) comprised of a liquid-permeable topsheet (4), a liquid-impermeable backsheet (5) and a mass of absorbent material (6) sandwiched therebetween, (b) each body (2, 3) having spaced apart side edges, each side edge of said front body (2) being detachably joined in overlapping relationship to a side edge of said rear body (3) by a plurality of fasteners (13), (c) each body (2, 3) having bottom edges, portions of the bottom edges of said bodies (2,3) being spaced apart from each other to form leg openings (10) and the remaining portions of the bottom edges of said bodies (2,3) being bonded together along a convexly curved welding line (8) to thereby form a convexly curved crotch zone that extends between said leg openings (10), said convexly curved crotch zone having an apex (9) that is closer to said waist opening than are said leg openings (10), (d) said liquid-absorbent panel (15) having a generally U-shaped configuration
  (i) that is positioned only in said crotch zone and permanently attached to the interior surface of said pants,
  (ii) the open ends of said U-shaped configuration facing toward said waist opening being located only in said crotch zone, a thickness of each of said open ends being smaller than that of the remaining portion of said liquid-absorbent panel (15)
  (iii) the closed end of said U-shaped configuration being mounted so as to float at a spaced distance from said convexly curved welding line (8) of said convexly curved crotch zone.

\* \* \* \* \*